United States Patent [19]

Carlesimo et al.

[11] Patent Number: 5,474,513
[45] Date of Patent: Dec. 12, 1995

[54] THERAPEUTIC EXERCISE APPARATUS

[76] Inventors: Michael O. Carlesimo, 4035 Overhill Ave., Norridge, Ill. 60634; Charles P. Ebey, 150 S. LaLonde Ave., Addison, Ill. 60101

[21] Appl. No.: 110,565

[22] Filed: Aug. 23, 1993

[51] Int. Cl.$^6$ .................................................. A63B 26/00
[52] U.S. Cl. ........................... 482/140; 482/142; 606/240
[58] Field of Search ..................................... 482/140, 142, 482/104; 606/240; 5/621, 622, 624, 633, 648; D6/596, 593, 599, 601; D24/190, 191; 297/464, DIG. 8

[56] References Cited

U.S. PATENT DOCUMENTS

| | | |
|---|---|---|
| D. 47,140 | 3/1915 | Newkirk . |
| D. 114,973 | 5/1939 | Eckman . |
| D. 117,862 | 11/1939 | Bauer . |
| D. 167,514 | 8/1952 | Hicks . |
| D. 167,666 | 9/1952 | Argento . |
| D. 203,251 | 12/1965 | Barber . |
| D. 207,315 | 4/1967 | Radford . |
| D. 209,118 | 10/1967 | Grube . |
| D. 211,721 | 7/1968 | Radford . |
| D. 215,536 | 10/1969 | Larsen . |
| D. 226,601 | 4/1973 | Klotzbach . |
| D. 233,200 | 10/1974 | Madl . |
| D. 242,388 | 11/1976 | Castleberry . |
| D. 246,816 | 1/1978 | Tam et al. . |
| D. 247,209 | 2/1978 | Woog . |
| D. 254,029 | 1/1980 | Barbagallo . |
| D. 255,959 | 7/1980 | Mitchell . |
| D. 263,439 | 3/1982 | Grube . |
| D. 271,647 | 12/1983 | McLeod . |
| D. 274,576 | 7/1984 | Tiffany . |
| D. 276,938 | 12/1984 | Pedersen . |
| D. 277,316 | 1/1985 | Meares . |
| D. 282,803 | 3/1986 | Righini . |
| D. 282,990 | 3/1986 | Sims et al. ............................ D6/596 |
| D. 284,032 | 5/1986 | Wahl et al. . |
| D. 284,724 | 7/1986 | Clark et al. . |
| D. 288,632 | 3/1987 | Grimsrud . |
| D. 292,460 | 10/1987 | Malin . |
| D. 292,767 | 11/1987 | Challen . |
| D. 293,755 | 1/1988 | Murphy . |
| D. 296,403 | 6/1988 | Palm . |
| D. 299,297 | 1/1989 | Prager . |
| D. 299,988 | 2/1989 | Parabita . |

(List continued on next page.)

FOREIGN PATENT DOCUMENTS

| | | | |
|---|---|---|---|
| 2634119 | 1/1990 | France | ................................ 606/240 |
| 452283 | 11/1927 | Germany . | |
| 3326078A1 | 1/1985 | Germany . | |

Primary Examiner—Richard J. Apley
Assistant Examiner—Jeanne M. Clark
Attorney, Agent, or Firm—Fitch, Even, Tabin & Flannery

[57] ABSTRACT

In accordance with the present invention, there is provided a therapeutic exercise device having a polyhedral foam body. The body may comprise a bottom side, a front side, a rear side, a left side, and a right side for supporting a top side. The top side may include a sloping surface and a plurality of arcuate surfaces cooperating to properly support and position an exerciser's legs, pelvic region and spinal vertebrae system to develop and maintain the musculoskeletal system.

The sloping and arcuate surfaces comprise a first outward convex surface which has a first maximum vertical height for supporting and positioning a persons legs, the sloping surface interconnects the first outward convex surface with the inward concave surface and supports and positions a person's legs with a predetermined orientation, the inward concave surface has a minimum vertical height value and positions and supports the person's buttocks with a predetermined angular orientation, and a second outward convex surface has a second vertical height and varying radius of curvature values for supporting and positioning a person's spinal vertebrae system when it is arched over the surface. The maximum vertical height of the second outward convex surface is spaced from the inward concave surface to ensure that the spinal vertebrae system arches thereover.

2 Claims, 4 Drawing Sheets

U.S. PATENT DOCUMENTS

| | | |
|---|---|---|
| D. 309,543 | 7/1990 | Goodman . |
| D. 310,312 | 9/1990 | Wong et al. . |
| D. 310,609 | 9/1990 | Burkhardt . |
| D. 312,372 | 11/1990 | Rutherford . |
| D. 317,840 | 7/1991 | Jagdat . |
| D. 318,392 | 7/1991 | Edelson . |
| D. 319,365 | 8/1991 | Edelson . |
| D. 321,760 | 11/1991 | Carney . |
| 1,904,039 | 4/1933 | Bruder . |
| 3,003,815 | 10/1961 | Zinn . |
| 3,555,582 | 1/1971 | Radford .................................... 5/633 |
| 3,953,072 | 4/1976 | Esquivel . |
| 4,027,888 | 6/1977 | Wilcox . |
| 4,193,150 | 3/1980 | Vineberg . |
| 4,206,524 | 6/1980 | Cook . |
| 4,230,099 | 10/1980 | Richardson .......................... 606/240 |
| 4,475,542 | 10/1984 | Brossard . |
| 4,484,781 | 11/1984 | Phelps . |
| 4,635,306 | 1/1987 | Willey . |
| 4,840,362 | 6/1989 | Boemer et al. ............................ 5/621 |
| 4,900,089 | 2/1990 | Alexander . |
| 5,054,142 | 10/1991 | Owens ...................................... 5/633 |
| 5,207,704 | 5/1993 | Shields .................................. 606/240 |

THERAPEUTIC EXERCISE APPARATUS

FIELD OF THE INVENTION

The present invention relates generally to exercise devices and, more particularly, to a therapeutic device for exercising and maintaining a person's musculoskeletal system.

BACKGROUND OF THE INVENTION

A wide variety of exercise methods and devices have been developed for exercising one's musculature system and, in particular, a person's trunk region musculature system, such as the abdominal and back muscles. In addition, therapeutic devices have been developed for stretching a person's spinal vertebrae system, including the corresponding muscles and ligaments. However, many of such devices concentrate on one or the other and fail to provide adequately a device which simultaneously exercises and maintains the entire musculoskeletal system of the trunk region in an acceptable manner.

A traditional method for exercising the muscles of the trunk region includes performing forward sit-ups on a planar surface, such as the floor. This is done from a starting position in which one lies on their back on the floor with their knees bent upward. To exercise, one raises their shoulders to curl upward toward the knees and then back down toward the floor. This motion is repetitiously performed as many times as desired.

With another method, an exercise device commonly known as an "incline board" is used to assist in performing forward sit-ups. This device includes a substantially planar board that is attached at one end to an upward extending stand to be inclined at a selected angle. To exercise with the incline board, one hooks their feet with a feet securing means located at the inclined end and lies upside down on the board. From this position, one then repetitiously curls upward and backward to perform sit-ups. Also, in some instances the boards are covered with a flexible pad to provide comfort.

Another exercise device includes a plastic dish shaped apparatus in which one sits for performing sit-ups. To exercise with this device, one places it on the floor and sits in it. The device positions and maintains one's pelvic girdle at a particular angle with respect to the floor and retrains it against movement from such position. Then, one repetitiously curls forward and backward to perform situps.

A further exercise device is typically known as a "Roman Chair" and includes a base from which two vertical members extend upward and parallel to one another. One supports a pedestal, upon which the person lies, and the other to support means for securing one's feet. To exercise with such device, one positions either their front pelvic region, for primarily working back muscles, or their buttocks, for primarily working front abdominal muscles, on the pedestal and hooks there feet under the securing means. In this position, one is extending freely like a cantilever from the pedestal and pivots upward and downward therefrom about the pedestal to exercise certain muscles.

With respect to the above exercise devices, they tend to be unsatisfactory for a number of reasons, which include the following. First, some provide hard, or moderately padded, surfaces upon which one exercises and, as a result, tend to be uncomfortable and tend to fail to absorb the impact of one's body during exercise.

Second, they fail to support properly the body for promoting safe and effective extension of the spinal vertebrae system while exercising. Such failure inclines to apply undue stress or pressure on the spinal vertebrae system.

In particular, the spinal vertebrae system is not a rigid unit, rather is built on a succession of vertebrae segments, which include the lumbar segment, the thoracic segment and the cervical segment. In profile, the vertebrae system takes on an "S" shape, and as soon as the vertebrae system is compelled to bend due to muscle exercise, the individual vertebrae of the different segments articulate, such as rotate, differently. For instance, some of the above exercise devices fail to consider that the lumbar vertebrae are not designed to arch as much as the thoracic vertebrae. Among being uncomfortable, failure to support the vertebrae system properly may be dangerous to the vertebrae system.

Finally, these exercise devices sometimes tend to concentrate on muscle maintenance and not on maintaining the spinal vertebrae system.

On the other hand, one known therapeutic device includes a large ball to perform a trunk stabilization and balance exercise for stretching one's spinal vertebrae system and associated muscles and ligaments. This device is a large ball over which one arches, either on their stomach or their back, to stretch their spinal vertebrae system and corresponding muscles and ligaments. This therapeutic device tends to be unsatisfactory because its primary purpose is to stretch, and not to develop and exercise the musculature system. Further, it requires another person's assistance because it is awkward to use and because it may be free to roll and one could easily roll off. Overall, it tends to concentrate on stretching and not on muscle maintenance.

Thus, there is a need for a therapeutic exercise device that not only exercises and maintains the muscles, but that exercises and maintains the entire musculoskeletal system of the trunk region.

In order to be commercially successful, the exercise device is preferably relatively light in weight, inexpensive and capable of being easily stored and transported from a place of storage to a place of use.

A general object of the present invention is to provide a therapeutic exercise device that exercises the entire musculoskeletal system of the trunk which is safe and effective to use.

Another object is to provide a therapeutic exercise device which supports the spine in a manner that deviates stress points.

A further object is to provide a therapeutic exercise device which is lightweight, highly durable, efficient, and cost effective to manufacture.

SUMMARY OF THE INVENTION

In accordance with the present invention, there is provided a lightweight, durable, therapeutic exercise device having a supporting body for supporting a top side which has a substantially continuous upper surface. The continuous upper surface includes a plurality of arcuate surface regions which cooperate to effectively support and position a person's body while performing exercises to develop and maintain entirely a selected region of a person's musculoskeletal system.

In the preferred embodiment, the supporting body may be formed from a flexible, resilient, cellular material capable of supporting the person's body at the upper surface to provide impact relief to the body during exercise use. In particular, the preferred body is formed to have a polyhedral body configuration comprising four sides which include a bottom side, a left side, a right side, a front side, a rear side and the top side. The preferred construction is a lightweight, one-piece block of a foamed plastic or rubber that has a contoured top surface to receive a person's body and to cushion and support the spine during stretching exercises.

More specifically, the upper contoured surface of the block body comprises a first outward convex surface region for supporting and positioning at least a portion of one of the legs of the person with a predetermined orientation, such as upward to bend the knees. Accordingly, the convex surface region has a first predetermined maximum vertical height which enables the person to effectively position their feet on the ground when draped over it. The upper surface also comprises a second outward convex surface region having varying radius of curvatures for effectively supporting and enabling the person's spinal vertebrae system to arch over and includes a second predetermined maximum vertical height.

In addition, the upper contoured surface comprises an inward convex surface region which is located intermediate the first outward convex surface region and the second outward convex surface region. This inward convex surface region communicates with the second outward convex surface region and supports the person's buttocks and positions the person's pelvic girdle in a predetermined angular orientation with respect to the bottom side of the apparatus and has a predetermined minimum vertical height. The structure and function of the inward concave surface region is to maintain the buttocks stationary and the pelvic girdle at this predetermined angular orientation throughout the exercise.

In particular, the second predetermined maximum vertical height is greater than the first predetermined maximum vertical height, and the second and first predetermined maximum vertical heights are greater than the predetermined minimum vertical height. Also, the second outward convex surface region at the second predetermined maximum vertical height is spaced from the inward convex surface region a predetermined distance so that the person's spinal vertebrae system is capable of arching over the second outward convex surface region while exercising.

The upper contoured surface may further comprise a sloping surface region interconnecting the first outward convex surface region and the inner concave surface region. This sloping surface region cooperates with the first outward convex surface region to assist in supporting and positioning the portion of at least one of the legs of the person in an upward direction and for cooperating with the inward concave surface region to assist in supporting and positioning the person's pelvic girdle in the predetermined angular orientation.

The apparatus is primarily designed for use in performing two therapeutic exercises which include forward flexion exercises, commonly known as sit-ups, and lateral flexion exercises, commonly known as side sit-ups. More specifically, to perform forward flexion exercises, the exerciser sits in the apparatus facing longitudinally toward the first outward convex surface region and drapes their legs thereover. To exercise, the exerciser arches backward over the second outward convex surface region. After arching backward, the exerciser curls forward to the upright starting position.

To perform lateral flexion exercises, the exerciser sits in the apparatus facing laterally and drapes their upper leg over the first outward convex surface region and their lower leg extends laterally away from the apparatus. To exercise, the exerciser arches sideways over the second outward convex surface region, and after arching sideways, the exerciser curls sideways back to the upright starting position. When performing such exercises to maintain one's musculoskeletal system, the surface areas pre-selectively support, absorb and stretch certain portions of one's musculoskeletal system.

By repeating either the forward or lateral flexion exercises for a predetermined number of repetitions, the musculoskeletal system of the trunk region are exercised to increase flexibility and durability.

In an alternative embodiment, the device may have a supporting body which supports an upper surface designed primarily for performing lateral flexion exercises. This body may be formed from a similar flexible, resilient cellular material capable of absorbing body impact at the upper surface.

In particular, the upper contoured surface comprises at least two arcuate surface regions for effectively supporting and positioning the person's body while performing exercises. These surfaces include an inward convex surface region having a predetermined minimum vertical height. This inward convex surface region supports the buttocks and positions the pelvic girdle at a predetermined starting angle with respect to a horizontal reference plane that is tangential to the inward convex surface at the minimum vertical height for starting the exercise. The structure and function of this surface region also allows the pelvic girdle to rotate from this starting angle through a predetermined angular range with respect to the horizontal reference plane during exercise. Additionally, the upper surface comprises an outward convex surface region for supporting the pelvic girdle during exercise and for cooperating with the inward convex surface region to allow the pelvic girdle to rotate through the predetermined angular range during exercise.

This outward convex surface region includes a first end surface region communicating with the inward concave surface region, a second end surface region located opposite the first end surface region and a predetermined maximum vertical height located between the first end surface region and the second end surface region.

In particular, the predetermined maximum vertical height is greater than the predetermined minimum vertical height. Also, the second end surface region is spaced from the inward concave surface region a predetermined distance to correspond to the iliac crest of the person when extended over the outward convex surface region during exercise.

Also in accordance with the present invention, the upper surface of the alternative embodiment may further comprises an inward concave groove surface region extending laterally about the outward convex surface region. This groove surface region may support and position the pelvic girdle during exercise while cooperating with the outward convex surface region and the inward concave surface region to allow the pelvic girdle to rotate from the starting angle through the predetermined angular range during exercise.

To perform lateral flexion exercises with the alternative embodiment, the exerciser sits in the apparatus facing laterally with both legs also extending laterally from the apparatus. To exercise, exerciser has the upper leg secured against vertical movement, such as by hooking it under an item of furniture. From this starting position, the exerciser extends downward toward the floor while curling about the outward convex surface region. While extending downward, the apparatus enables the pelvic girdle to rotate so the exerciser can rotate to extend substantially parallel to the floor. Next, the exerciser curls back upward to the starting position, and repeats this sequence for a desired number of repetitions. This exercise is performed for the other side by facing in the opposite direction.

BRIEF DESCRIPTION OF THE DRAWINGS

The present invention will be described in connection with the accompanying drawings, which illustrate the preferred embodiment and details of the invention, and in which.

DETAILED DESCRIPTION OF THE PREFERRED EMBODIMENT

Figure 1:
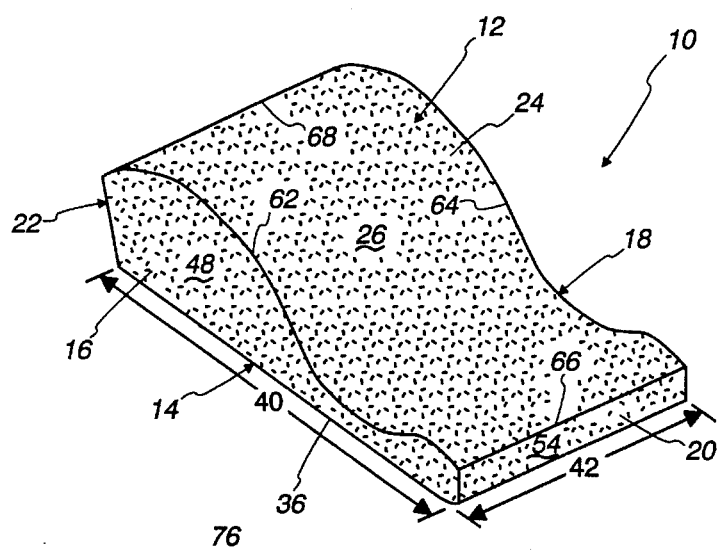
FIG. 1 is a perspective view of a therapeutic exercise apparatus embodying the present invention.

As shown in the drawings for purpose of illustration, the invention is preferably embodied in a therapeutic exercise apparatus 10 for simultaneously exercising and maintaining a person's trunk and neck musculoskeletal system within the normal physiological limits of the spinal vertebrae system. In the illustrated embodiment of FIG. 1, the exercise apparatus 10 includes a polyhedral body 12 formed of a non-allergenic, flexible, resilient cellular material such as, for example, natural or synthetic rubber sponge or foam, ether foam, polyester foam, polyurethane foam and the like.

The preferred body 12 is block-shaped and is formed of rubber foam comprised of ether 2.8 density 35 I.L.D. 2835. With this density, 35 pounds of pressure forces the foam down about one inch. Using such resilient cellular material renders the apparatus capable of cushioning the person's body to provide relief to the body during exercise. However, other foam compositions having different or varying density properties may be employed to provide different levels of softness or hardness to cushion one's body, such as ether foam rubber having 2.8 density 60 I.L.D. (2860) or 1.8 density 35 I.L.D. (1835). The selection of a given density may depend on the user's weight and level of comfort.

Figure 4:
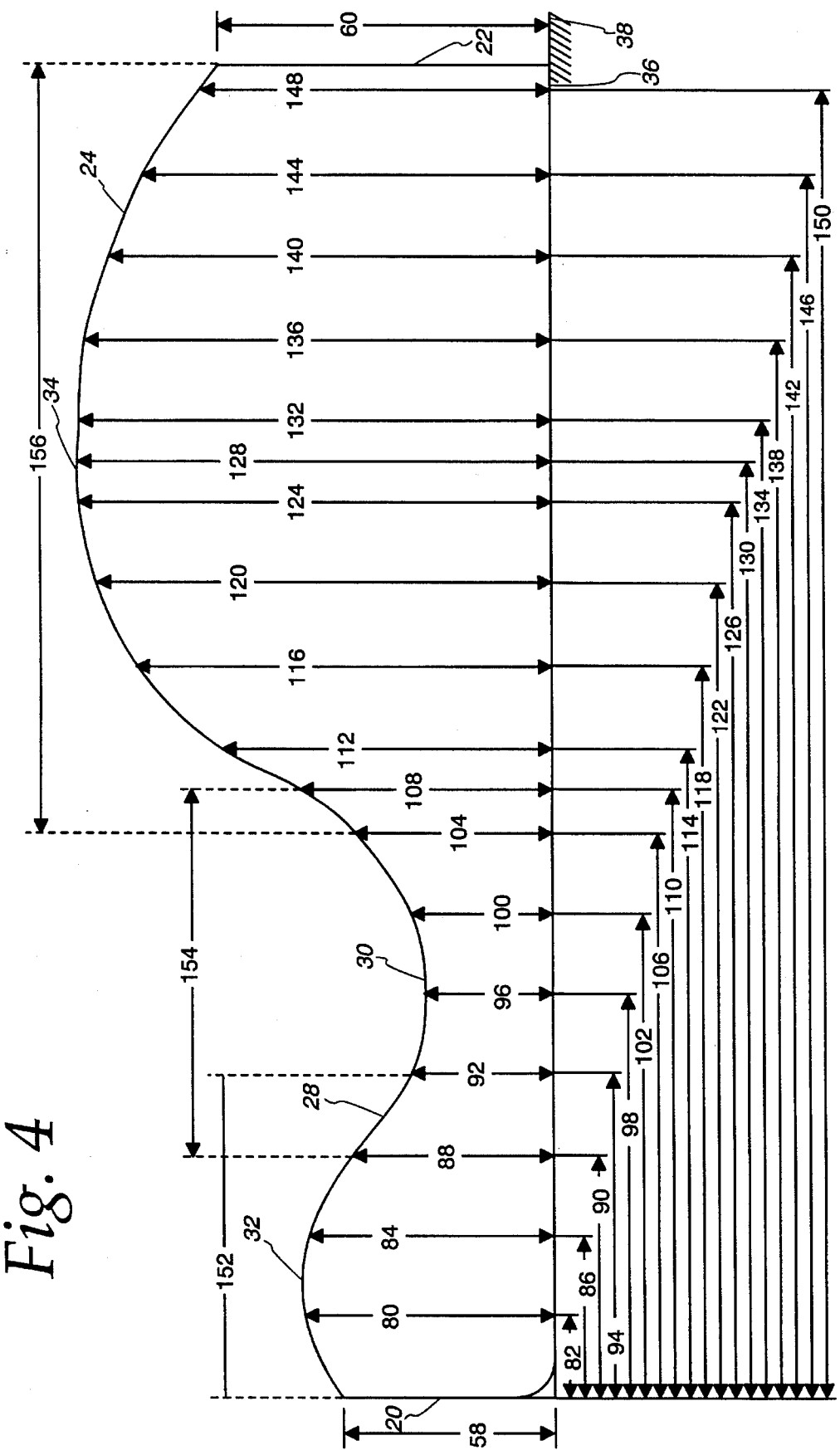
FIG. 4 is left side elevational view of the apparatus of FIG. 1 illustrating in detail the upper surface.

As best illustrated in FIG. 1, the body 12 comprises four sides which include a bottom 14, a left side 16, a right side 18, a front side 20, a rear side 22 and a top side 24. A primary structure and function of the body 12 is for supporting the top side 24. For properly supporting one's spinal vertebrae system, the top side 24 includes a continuous, contoured surface 26. As illustrated in FIG. 4, the surface 26 comprises a sloping surface region 28, an inward concave surface region 30 and a pair of outward convex surface regions 32 and 34.

Since the structure and function of the body is for supporting the top side and its continuous non-planar surface, the body alternatively may have a support construction, such as a hollow shell construction or an air bag construction, having, or supporting, the above-described top side. The hollow shell construction may be made from different materials, such as plastic, wood or metal and, depending on the material, may include a number of vertical and lateral support braces to support the top side. The top side also may be covered with a foam pad made from one of the above-mentioned foam materials and the like.

Returning to the preferred foam body 12 for supporting the top side 24, the bottom 14 is rectangular in configuration and includes an outer planar bottom surface 36, which engages a ground or floor area 38 (FIG. 4) for supporting the exercise apparatus 10 during use. In this respect, the surface 36 provides some frictional engagement with the ground area 38 to prevent the body 12 from sliding during use. The preferred bottom 14 includes a predetermined longitudinal length value, reference number 40, and a lateral width value, reference number 42, which, in the preferred embodiment, are about 33½ inches and 17 inches, respectively. Although the present invention is not limited to any particular size or construction, the one block of contoured foam provides an inexpensive construction which is lightweight and of a size that can be easily transported and stored when not in use.

The left and right sides 16 and 18 are identical in structure and function, and as illustrated by left side 16, each includes an outer substantially planar side surface 48, which extends vertically from the bottom 14 to terminate with a continuous upper arcuate edge 62, that defines in part the continuous non-planar surface 26. In particular, both sides 16 and 18 include a predetermined length value, which is identical to that of the bottom 14, reference number 40. With respect to the ground area 38, both the left and right sides 16 and 18 include varying height values which alter in accordance with varying vertical height values of the continuous non-planar surface 26, which is described infra regarding the top side 24.

As illustrated by front side 20, both the front and rear sides 20 and 22 include an outer substantially planar surface 54 and a predetermined width value, which is identical to that of the bottom 14, reference number 42. The front and rear sides 20 and 22 include different vertical height values, reference numbers 58 and 60 (FIG. 4), with respect to the ground area 38, and in which, the vertical height of the rear side 22 is greater than that for the front side 20. In the preferred embodiment, the vertical height values, reference numbers 58 and 60, are about 5⅜ inches and 8¼ inches, respectively.

The top side 24 is defined at its perimeter by edges 62, 64, 66 and 68, which are also the upper edges of the left and right sides 16 and 18 and the front and rear sides 20 and 22, respectively. As a result, the top side 24 interconnects the left and right sides 16 and 18 and the front and rear sides 20 and 22. The top side 24 has a predetermined width value, which is identical to the bottom side 14 and the front and back sides 20 and 22, reference number 42.

Figure 2:
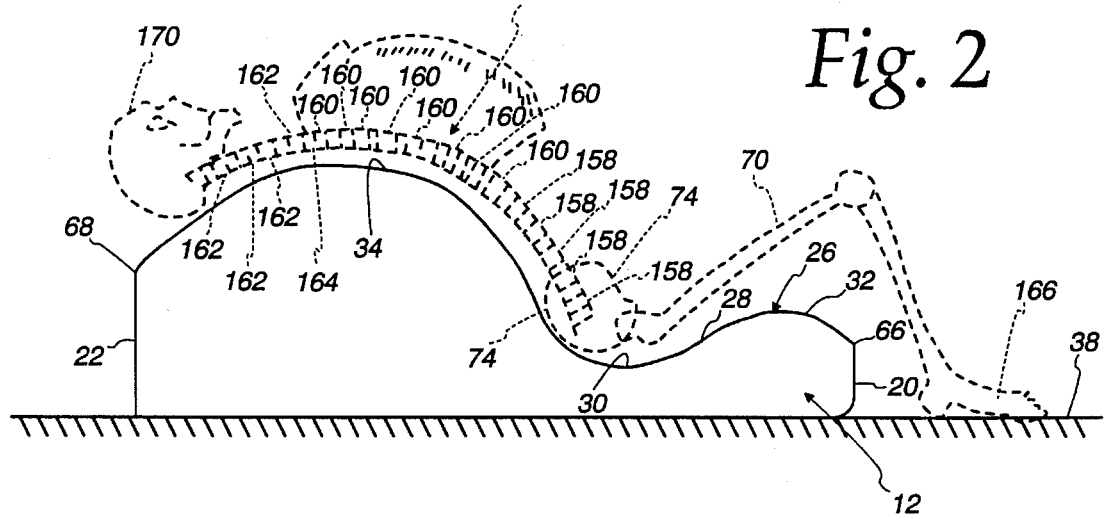
FIG. 2 is a left side elevational view of the apparatus of FIG. 1 illustrating a person performing a forward flexion exercise.

For effectively supporting and positioning one's body while exercising with the apparatus 10, the top side 24 includes the continuous contoured surface 26. As illustrated in FIG. 2, proceeding from the front edge 66 to the rear edge 68 of the top side 24, the non-planar surface 26 comprises the first outward convex surface region 32 for supporting and positioning at least a portion of one of the body's legs 70 and 72, the downward sloping surface region 28 also for supporting and positioning at least a portion of one of the body's legs 70 and 72 at a predetermined angular orientation, the inward concave surface region 30 for cooperating with the sloping surface region 28 for effectively supporting and positioning the body's buttocks 74, and the second outward convex surface region 34 for effectively supporting and positioning the body's spinal vertebrae system 76 such as along a marked path.

With both the outer convex surface regions 32 and 34 and the inner concave surface region 30 having varying radius of curvature values in order to effectively support certain body segments, each will be described with vertical height values measured from the ground area 38 that correspond to longitudinal distance values measured from the front side 20, as illustrated in FIG. 4.

For supporting and positioning at least a portion of one of the body's legs 70 and 72, the first outward convex surface region 32 has predetermined vertical height values, reference numbers 80, 84 and 88, with respect to the ground area 38, which correspond in order to predetermined distance values, reference numbers 82, 86 and 90, from the front side 20. By way of example, the preferred vertical height values 80, 84 and 88 are approximately 6³⁄₁₆ inches, 6⅛ inches and 5¹⁄₁₆ inches, respectively, and correspond in order to distance values 82, 86 and 90, which are approximately 2 inches, 4 inches and 6 inches, respectively.

To further support and position at least a portion of one's legs at a safe and effective orientation with respect to the ground 38, the sloping surface region 28 is substantially planar and interconnects the first outward convex surface region 32 with the inward concave surface region 30 at a first and second intersection region, illustrated by distance value reference numbers 90 and 94 (FIG. 4), respectively. In effect, the first outward convex surface region 32 and the sloping surface region 28 cooperate to form a leg support portion, reference number 152, for supporting and positioning at least a portion of one's legs 70, 72.

For supporting and positioning one's buttocks and pelvic girdle 74, a buttocks support portion, reference number 154, is formed from the sloping surface region 28 cooperating with the inward concave surface region 30. In particular, the inward concave surface region 30 has predetermined vertical height values, reference numbers 92, 96, 100, 104 and 108, with respect to the ground area 38, which correspond in order to predetermined distance values, reference numbers 94, 98, 102, 106 and 110, from the front side 20. By way of example, the preferred vertical height values 92, 96, 100, 104 and 108 are approximately 3⁹⁄₁₆ inches, 3⅛ inches, 3⁹⁄₁₆ inches, 5 inches and 6¹³⁄₁₆ inches, respectively, and correspond in order to reference distance values 94, 98, 102, 106 and 110, which are approximately 8 inches, 10 inches, 12 inches, 14 inches and 15 inches, respectively.

In particular, at reference distance value 110, the inward concave surface region 30 intersects the second outward concave surface region 34. The inward concave surface region 30 and the second outward convex surface region 34 cooperate to form a spinal vertebra system support region 156.

For effectively supporting and positioning the spinal vertebra system 76 along a marked path, the second outward convex surface region 34 has predetermined vertical height values, reference numbers 112, 116, 120, 124, 128, 132, 136, 140, 144 and 148, with respect to the ground area 38, which correspond in order to predetermined distance values, reference numbers 114, 118, 122, 126, 130, 134, 138, 142, 146 and 150, from the front side 20. By way of example, the preferred vertical height values 112, 116, 120, 124, 128, 132, 136, 140, 144 and 148 are approximately 8⁷⁄₁₆ inches, 10³⁄₁₆ inches, 11⅛ inches, 11½ inches, 11⁹⁄₁₆ inches, 11⁹⁄₁₆ inches, 11⅜ inches, 10⅞ inches, 10⅛ inches and 8¾ inches, respectively, and correspond in order to reference distance values 114, 118, 122, 126, 130, 134, 138, 142, 146 and 150, which are approximately 16 inches, 18 inches, 20 inches, 22 inches, 23 inches, 24 inches, 26 inches, 28 inches, 30 inches and 32 inches, respectively. In particular, the second outward convex surface region 34 has a maximum height at reference numbers 128 and 132, and it is this maximum height surface region which is spaced a predetermined distance from the inner concave surface region 30 in order to ensure that the spinal vertebrae system 76 extends over the second outward convex surface region 34 during exercise.

All the surfaces, especially the surface regions of the top side 24, may be provided with a coating of a synthetic polymer such as for example, a silicone polymer, a polyacrylic acid ester, a polymethacrylic acid ester, a polyurethane and the like. The coating should facilitate washing and contribute to the toughness of the surface to prevent easy rupturing, penetration or deterioration of the surfaces. Alternatively, a cover which is made of washable material, such as a fabric, may by used to cover the apparatus. The cover would have a like configuration as the body 12 in order to fit the body tightly with a glove-like fit.

In accordance with the present invention, the apparatus 10 is designed to exercise one's trunk and lower limb musculature and to maintain normal joint motion throughout the entire spinal vertebrae system 76, which includes segments of lumbar vertebrae 158, thoracic vertebrae 160 and the cervical vertebrae 162, a shoulder girdle 164 and the buttocks or pelvic girdle 74, as illustrated in FIG. 2.

In particular, the apparatus 10 is designed for performing primarily two exercises to maintain muscle tone and spinal flexibility and to engender durability and flexibility of the total musculoskeletal system. The two exercises include forward flexion exercises (FIG. 2), commonly known as sit-ups, which help develop, in general, the back and abdominal muscles and lateral flexion exercises (FIG. 3), commonly known as side sit-ups, which help develop the lateral abdominal and back muscles. When performing the above exercises, the apparatus 10 relieves pressure and/or stress on the spinal vertebrae system 76, by providing it with a marked position during exercise.

As illustrated in FIG. 2, with reference to FIG. 4, when the apparatus 10 is used to perform forward flexion exercise, its design exercises a plurality of muscles including, but not limited thereto: muscles of the abdominal region and muscles located between the ribs which include, the internal and external obliques and the rectus abdominous; the trunk flexures including the iliopsoas and the psoas; the intercostal and the latissimus dorsi; the cervical musculature; the sternocleidomastoid; and the scaleni. In addition, it also exercises and stretches the anterior longitudinal ligaments and traction the spinal vertebrae segments.

In performing forward flexion exercise, one seats their buttocks or pelvic girdle 74 in the buttocks support portion 154 (FIG. 4) of the apparatus 10 to face longitudinally toward the front side 20 with respect to the body 12. The design of the support portion 154 supports the buttocks and positions the pelvic girdle 74 at a predetermined angle with respect to a horizontal plane that includes the bottom side 14. The predetermined angle is about 45 degrees in the preferred embodiment. When seated in this manner, one places their legs 70 and 72 so as to extend up the leg support portion 152 (FIG. 4), and since the first outward convex surface region 32 includes a predetermined maximum vertical height, the feet 166 and 168 are able to rest on the ground area 38. For an exercise starting position, one rests up against the second outward convex surface region 34. To exercise, one then arches back over the spinal vertebra support portion 156 (FIG. 4) to rest one's head 170 on the apparatus 10. This backward arching over the spinal vertebrae support portion 156 (FIG. 4) of the non-planar surface 26 safely and effectively exercises and maintains the musculoskeletal system of trunk and back region.

To exercise one muscles, including such muscles listed above, one bends, or curls, forward from the extended, arched position to a generally fetal like position, while remaining seated in the buttocks support portion 154 (FIG. 4), which restricts movement of the buttocks 74. The backward extension followed by this forward curl is repeated for a predetermined number of repetitions as desired.

Figure 3:
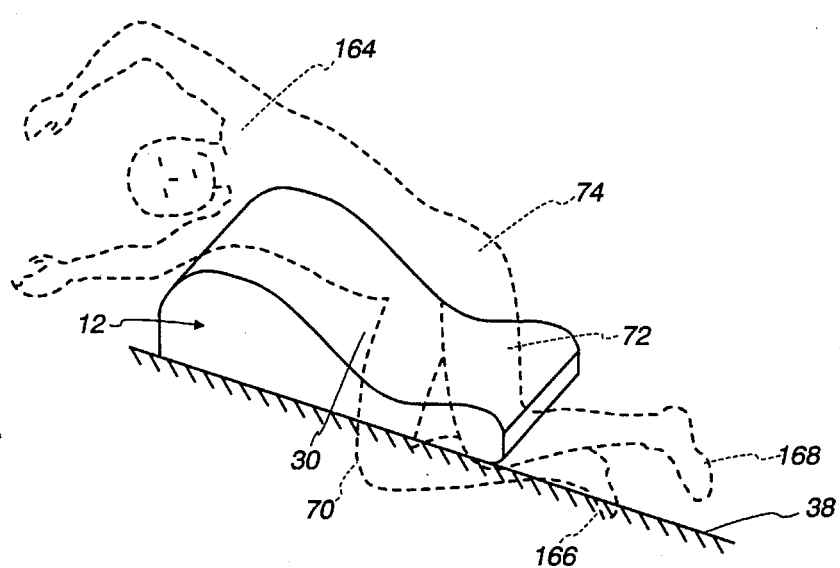
FIG. 3 is a perspective view of the apparatus of FIG. 1 illustrating a person performing a lateral flexion exercise.

As best illustrated by FIG. 3, with reference to FIG. 4, when the apparatus 10 is used to perform lateral flexion exercise, its design exercises a plurality of muscles including, but not limited thereto, muscles of the abdominal region and muscles located between the ribs which include, but not limited thereto, the latissimus, the erector spinae (iliocostalis, longissimus, spinalis), the quadratus lumborum, latissimus dorsi, psoas major, internal and external abdominal obliques, multifidus, trapezius, splenius, cervicises, rotatores, rhomboids, and levator scapula muscles. In addition, this exercises and stretches the interspinous ligaments and the inter-transverse ligaments.

In performing lateral flexion exercises, one seats their buttocks in the buttocks support portion 154 (FIG. 4) of the apparatus 10 to face transversely toward the left side 16, as illustrated, with respect to the body 12. When seated in this manner, one has one side of there pelvic girdle 74 against the buttocks support portion 154 (FIG. 4) and the other side of the hip is thereby exposed. This positions the pelvic girdle 74 at a predetermined angular orientation with respect to the bottom side 14. Also, one's legs preferably are positioned with one leg 70 extending out of the buttocks support portion 154 (FIG. 4) and the other leg 72 draped over the leg support surface portion 152 (FIG. 4), and the feet 166 and 168 rest on the ground area 38. The buttocks support portion 154 (FIG. 4) maintains the pelvic girdle 74 at an safe and effective upward angle with respect to the ground area 38.

One first rests the side of their trunk region against the spinal vertebrae support portion 156 (FIG. 4) and, then, arches further over this portion 156 (FIG. 4) to extend one's trunk musculoskeletal system, in particular, the lumbar vertebrae 158 and the thoracic vertebrae 160 and corresponding muscles and ligaments. In terminating this sideward arch, one rests their shoulder girdle 164 on the spinal vertebrae support portion 156 (FIG. 4).

To exercise the muscles, one bends, or curls, sideways from the extended position to a generally contracted position while remaining seated in the buttocks support portion 154 (FIG. 4). The sideward extension followed by this sideward curl is repeated for a predetermined number of repetitions as desired. Once finished with one side, the exerciser sits facing the other way in the apparatus 10 and performs the above described motions.

As illustrated in FIGS. 5 through 9, an alternative embodiment of the present invention is embraced in exercise apparatus 200. The exercise apparatus 200 is employed primarily for performing lateral flexion exercises (side sit-ups) to strengthen the erector spinae muscles, quadratus lamborum, lateral tensor fascia lata, and the abdominal muscles. The apparatus 200 is intended to operate in accordance with the principles of the first embodiment of apparatus 10. That is, it provides the exerciser with an exercise starting position in which the pelvis is supported at an angle of about 40 to 45 degrees with respect to the ground 38. This starting position provides for effective exercise of the above-mentioned ligaments and muscles. Thus, the alternative embodiment incorporates necessary aspects of the first embodiment of the apparatus 10 with the following modifications to use it for its desired purpose.

Figure 5:
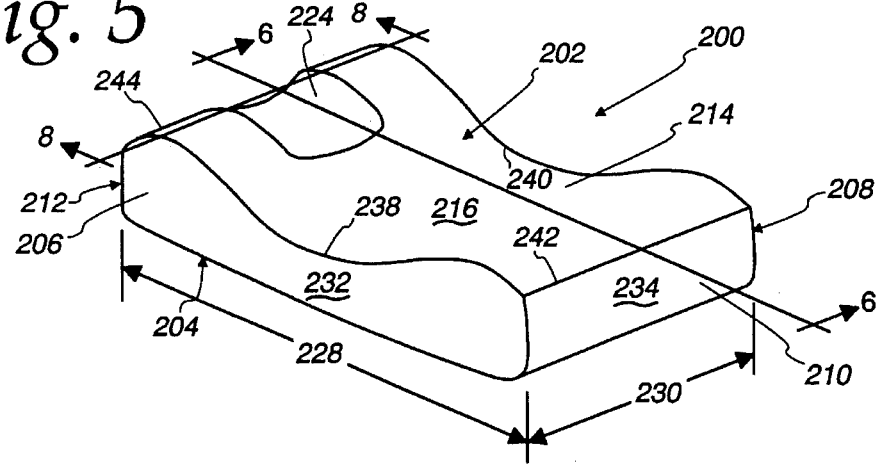
FIG. 5 is a perspective view of an alternative embodiment of an exercise apparatus embodying the present invention.

As best shown in FIG. 5, the exercise apparatus 200 includes a polyhedral body 202 formed preferably of rubber foam having similar characteristics as that of the body 12 of the first illustrated apparatus 10, including a rubber foam comprising ether 2.8 density 60 I.L.D. 2860, for providing slightly more support, but still maintaining its ability to allow the exerciser to melt into the foam rubber to provide support and comfort. That is, the foam body 202 provides impact relief from the exerciser's body during exercise. Also similar to body 12, the body 202 comprises four sides which include a bottom 204, a left side 206, a right side 208, a front side 210, a rear side 212 and a top side 214. The structure and function of the body 202 is primarily for supporting the top side 214. The top side 214 includes a continuous non-planar surface 216.

Figure 6:
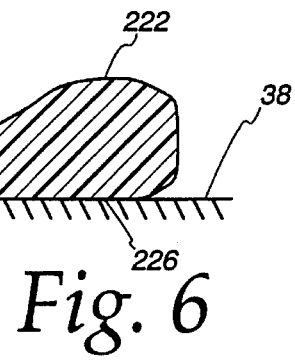
FIG. 6 is a cross-sectional view of the apparatus taken along line 6—6 of FIG. 5.

As best illustrated in FIG. 6, the non-planar surface 216 comprises an inward concave surface region 218 and a pair of outward convex surface regions 220 and 222 in which one of the outward convex surface regions such as region 220 may include a lateral groove 224. However, the groove 224 is not necessary for effective use of the apparatus 200. The outward convex surface region 220 positions the exerciser at an exercise starting angle of about 40 to 45 degrees which protects the pelvis and spinal vertebrae system throughout exercise performance, and the lateral groove 224 protects and positions the pelvic girdle and vertebrae spinal system when not in the starting position while performing exercises. Like the above described embodiment (apparatus 10), the exercises performed on the apparatus 200 are anatomically correct in being both functionally and mechanically correct for a normal healthy person.

The bottom 204 is rectangular in configuration and includes an outer planar bottom surface 226, which engages a ground or floor area 38 (FIG. 6) for supporting the exercise apparatus 200 during use. The preferred bottom 204 includes a predetermined longitudinal length value, reference number 228, and a lateral width value, reference number 230, which, in the preferred embodiment, are about 21 inches and 17 inches, respectively.

The left and right sides 206 and 208 are identical in structure and function, and as illustrated by left side 206, each includes an outer substantially planar side surface 232 and extends vertically from the bottom 204 to terminate with a continuous upper edge 238, that defines in part the continuous non-planar surface 216. Both sides 206 and 208 have a predetermined length value that is identical to that of the bottom 204, indicated by reference number 228. With respect to the bottom 204, both the left and right sides 206 and 208 include varying height values which is described infra regarding the top side 214.

As illustrated by front side 210, both the front and rear sides 210 and 212 include an outer substantially planar surface 234 having a predetermined width value, which is identical to that of the bottom 204, reference number 230. The front and rear sides 210 and 212 include identical vertical height values, reference number 236. In the preferred embodiment, the vertical height value reference number 236, is about 5⅛ inches.

The top side 214 is defined at its perimeter by upper edges 238, 240, 242 and 244, which are also the upper edges of the left and right sides 206 and 208 and the front and rear sides 210 and 212, respectively. Accordingly, the top side 214 interconnects the left and right sides 206 and 208 and the front and rear sides 210 and 212. The top side 214 includes a predetermined width value, which is identical to the that of the bottom 204 and the front and rear sides 210 and 212, and which is indicated by reference number 230.

Figure 7:
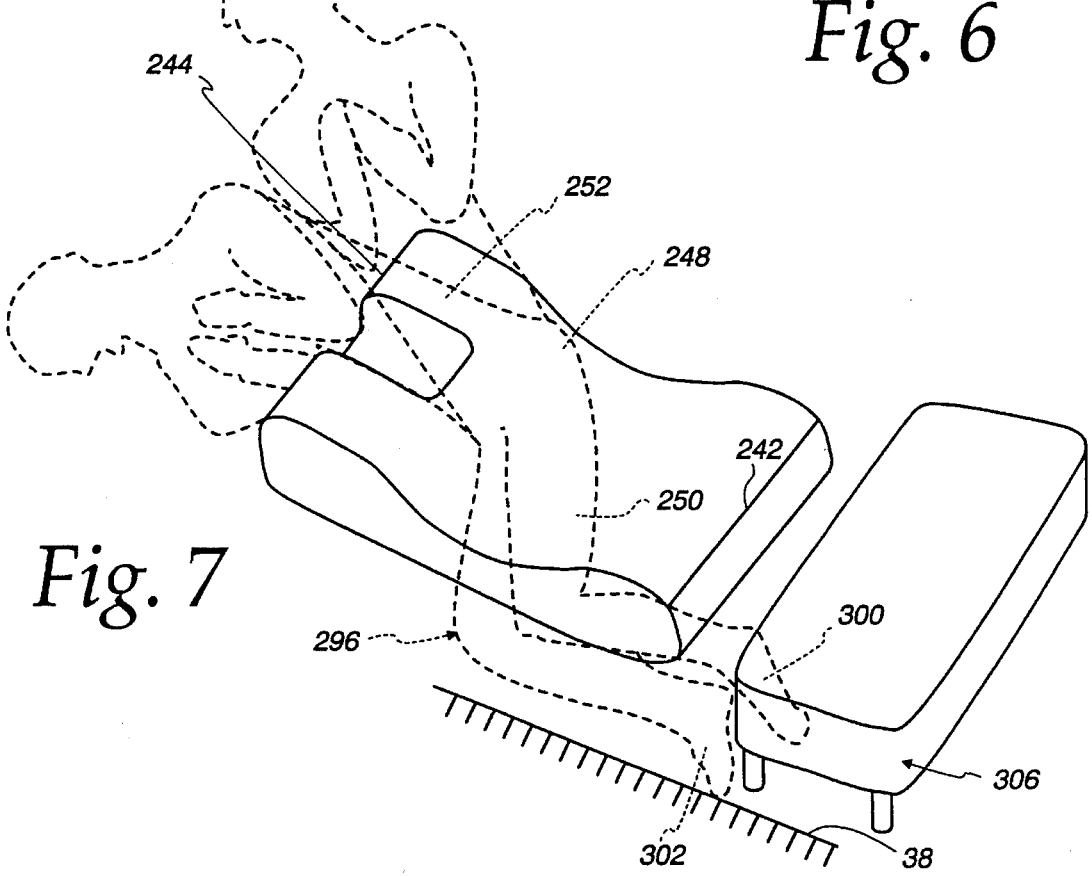
FIG. 7 is a perspective view of the apparatus of FIG. 5 illustrating a person performing a lateral flexion exercise.

For supporting one's body while exercising with the apparatus 200, the top side 214 is provided with the continuous non-planar surface 216. As best illustrated in FIG. 7, proceeding from the front edge 242 to the rear edge 244 of the top side 214, the non-planar surface 216 comprises the first outward convex surface region 220 for supporting one's pelvic girdle region 248 and femur 250 at a predetermined angle, which is approximately 40 to 45 degrees with respect to the ground when in the starting position, the inward concave surface region 218 for cooperating with the first outward convex surface region 220 for effectively supporting one's pelvic girdle region 248 and upper leg 250 at all times and the first outward convex surface region 220 which along with its groove 224 effectively supports the pelvic girdle region 248 and the iliac crest region 252 during exercise.

Figure 9:
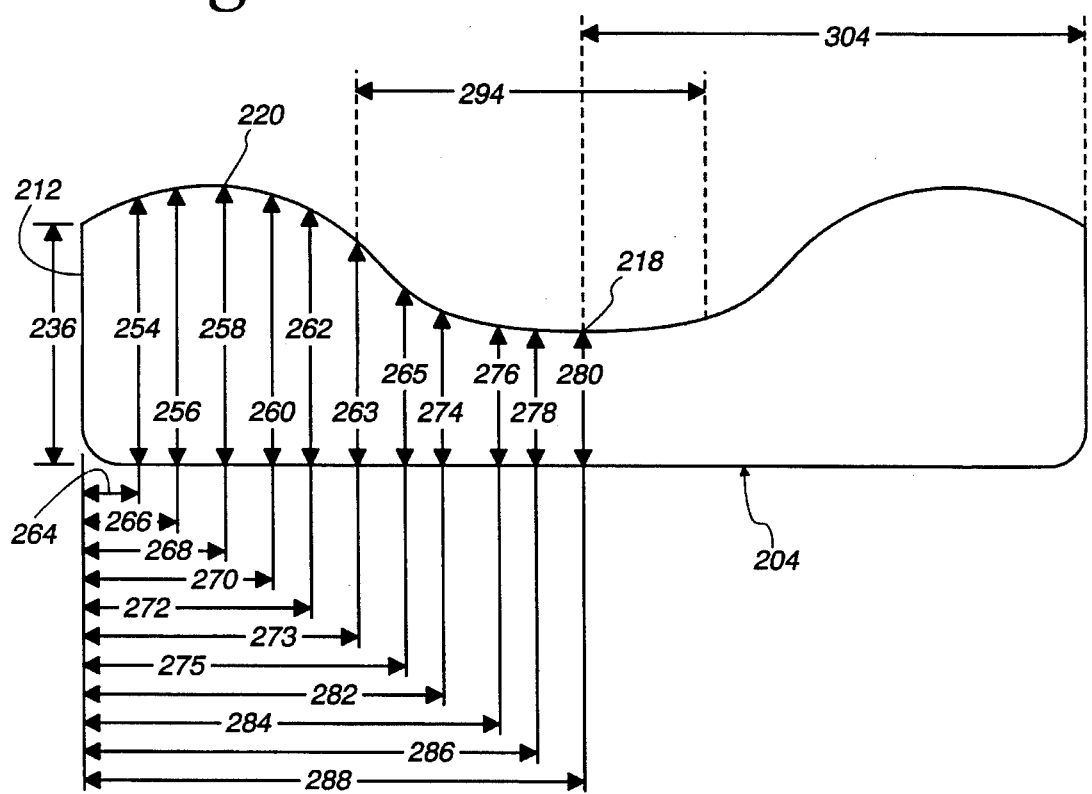
FIG. 9 is a left side elevational view of the apparatus of FIG. 5 illustrating in detail the upper surface.

Since both the outer convex surface regions 220 and 222 are identical and have varying radius of curvature values, as viewed from side elevation, and the inward convex surface region 218 has a constant radius of curvature, only the second outward convex surface region 222 and half the inward concave surface region 218 are described. These surface regions are described with vertical height values measured from the bottom 204 that correspond to longitudinal distance values measured from the rear side 212, as illustrated in FIG. 9.

The outward convex surface region 220 has predetermined vertical height values, reference numbers 254, 256, 258, 260, 262, 263 and 265, with respect to the bottom 204, which correspond in order to predetermined distance values, reference numbers 264, 266, 268, 270, 272, 273 and 275 from the rear side 212. By way of example, the preferred vertical height values 254, 256, 258, 260, 262, 263 and 265, are approximately 5¹¹⁄₁₆ inches, 5¹⁵⁄₁₆ inches, 6 inches, 5¹³⁄₁₆ inches, 5⁷⁄₁₆ inches, 4¹³⁄₁₆ inches and 3¹⁵⁄₁₆ inches, respectively, and correspond in order to distance values 264, 266, 268, 270, 272, 273 and 275, which are approximately 1 inch, 2 inches, 3 inches, 4 inches, 5 inches, 6 inches and 7 inches, respectively.

The inward concave surface region 218 has predetermined vertical height values, reference numbers 274, 276, 278 and 280, with respect to the bottom 204, which correspond in order to predetermined distance values, reference numbers 282, 284, 286 and 288, from the rear side 212. By way of example, the preferred vertical height values 274, 276, 278 and 280 are approximately 3³⁄₁₆ inches, 2¹³⁄₁₆ inches, 2¾ inches and 2¹¹⁄₁₆ inches, respectively, and correspond in order to distance values 282, 284, 286 and 288 which are approximately 8 inches, 9 inches, 10 inches and 10½ inches, respectively.

Figure 8:
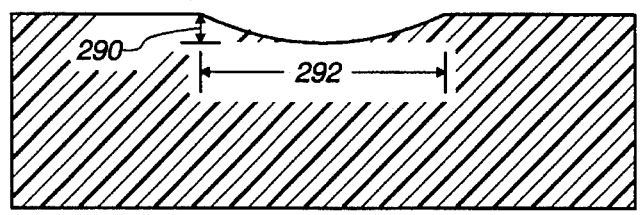
FIG. 8 is a cross-sectional view of the apparatus taken along line 8—8 of FIG. 5 illustrating a lateral groove.

As illustrated in FIGS. 5 and 8, if the groove 224 is desired, it is located laterally at a central position in the top side 214 at the second outward convex surface region 220 and extends longitudinally therethrough. The groove 224 entails a constant radius of curvature value to provide a predetermined maximum depth value, reference number 290, with respect to the top side 214 at reference number 266 (FIG. 9), and a predetermined maximum width value, reference number 292. In the preferred embodiment, the maximum depth value may range from ⅛ to ¾ inches, and the maximum width value is approximately 6 inches.

In accordance with the present invention, the apparatus 200 is designed to provide protection to the mechanical structures of the pelvis and spinal vertebrae system while performing side sit-ups to exercise and develop all the lateral abdominal muscles and the back muscles in accordance with all the natural laws of the spinal vertebrae system. As illustrated in FIG. 7, in performing side sit-ups, one sits in the buttocks support portion 294 of the apparatus 200 to face transversely toward the left side 206. If the apparatus 200 includes the lateral groove 224, it is located immediately to the right of the person's pelvis. When seated in this manner, one has one side of their pelvic girdle 248 against the buttocks support portion 294 and the other side of the hip is thereby exposed. Also, one's legs preferably are positioned with one leg 296 extending out of the buttocks support portion 294 and the other, upper leg 250 draped over the leg support portion 304, and the foot 300 of the upper leg 250 is anchored to a support 306, such as by hooking its toes under a piece of furniture, like a sofa, and the other foot 302 rests on the ground area 38 freely. This is the starting position. In this position, the buttocks support portion 294 maintains the pelvic girdle 248 at a predetermined angle with respect to the ground 38.

To perform an exercise, one arches sideways over the outward convex surface region 220 at the groove 224 while remaining seated in the buttocks portion 294. After this arch, one returns back to the upright starting position. This is then repeated for a predetermined number of repetitions as desired. Once finished with one side, the exerciser sits facing the other way in the apparatus 200 and performs the above described motions.

In accordance with the present invention, the foam construction of the buttocks support portion 294 gives support to the user, but allows the pelvic girdle 248 to roll and have free movement throughout the full arch of the side sit-up. In particular, as the exerciser arches laterally from the starting position over the second outward convex surface region 220, the pelvis rolls from the desired starting angle of about 40 to 45 degrees to an angle of about 65–70 degrees with respect to the vertical. The buttocks support portion 294 provides stability through the exercise without pinching the pelvis between the first and second outward convex portions 222 and 220.

In a third alternative embodiment, the apparatus 200 includes a second lateral groove in the top side at the other outward convex portion 222. This second lateral groove enables the apparatus 200 to be used to exercise the lower limbs (i.e., one's legs) in accordance with the present invention. When performing leg exercises, the apparatus acts as support for the pelvis. The exerciser sits in the apparatus the same way as if performing side sit-ups, as described above, and lays parallel to the ground keeping the one leg extending out of the buttocks portion 294, and the other upper leg extends through the second lateral groove. The curve of the outward convex surface region and second lateral groove provide for full support of the body. To exercise, one raises the upper leg vertically out of the second groove, and then back down into the groove. The exerciser performs the safe movement for the other leg by facing the other way.

However, one may also maintain both legs extended for leg exercises. This enables one to perform bilateral leg exercises. That is, it allows the exerciser to raise both legs simultaneously together.

Thus, it is apparent that there has been provided, in accordance with the invention, an exercise apparatus that fully satisfies the objects, aims and advantages set forth above. While the invention has been described in conjunction with a specific embodiment, it is evident that many alternatives, modifications and variations will be apparent to those skilled in the art in light of the foregoing descriptions.

What is claimed is:

1. An apparatus for use by a person to perform exercise essentially consisting of:

a elongated supporting body having an upper surface, a first end region, second end region and a lower surface adapted to contact a stationary supporting surface, said supporting body formed from a flexible, resilient material having substantial firmness to effectively support and position the person's body while performing side sit-up exercises;

the upper surface comprising an inward concave surface region having a first end and a second end and a predetermined minimum vertical height from the supporting surface substantially centrally located, and having a sufficient length and curvature adapted for supporting the buttocks and for positioning the pelvic girdle at a predetermined starting angle in the range of 40 to 45 degrees from a vertical plane perpendicular to the inward concave surface region at the minimum vertical height for starting the exercise and for allowing the pelvic girdle to rotate from the starting angle through a predetermined angular range to an angle in the range of 65 to 75 degrees from the vertical plane during exercise;

said inward concave surface region centrally located and extending along the longitudinal axis between said first and second end regions;

said supporting body further including a first and second outward convex surface regions integral with and continuously attached to said first and second ends of the inward concave surface region, respectively, said first and second outward convex surface regions each having a maximum vertical height from the supporting surface being higher than said minimum vertical height of the inward concave surface region, said first and second outward convex surface regions forming said first and second end regions, respectively;

said first outward convex surface region having a length along the longitudinal axis adapted to correspond to the length of the person's lower torso region and having an upper surface including an inward concave groove centrally located along and extending laterally about the longitudinal axis, said groove is sized and configured to accommodate the iliac crest of the person thereby providing proper support and positioning of the pelvic girdle during the exercise and allowing the pelvic girdle to rotate from the starting angle through the predetermined range during the side sit-up exercise.

2. An apparatus in accordance with claim 1 wherein the flexible, resilient material is ether foam rubber having a 2.8 density 60 I.L.D..

* * * * *